US011426361B2

(12) United States Patent
Dikstein

(10) Patent No.: US 11,426,361 B2
(45) Date of Patent: Aug. 30, 2022

(54) EYE DROPS FOR TREATMENT OF IRRITATION NOT DUE TO INFECTION

(71) Applicant: Resdevco Research and Development Co. Ltd., Jerusalem (IL)

(72) Inventor: Shabtay Dikstein, Jerusalem (IL)

(73) Assignee: Resdevco Research and Development Co. Ltd., Jerusalem (IL)

( * ) Notice: Subject to any disclaimer, the term of this patent is extended or adjusted under 35 U.S.C. 154(b) by 0 days.

(21) Appl. No.: 17/191,191

(22) Filed: Mar. 3, 2021

(65) Prior Publication Data
US 2021/0186892 A1 Jun. 24, 2021

Related U.S. Application Data

(63) Continuation of application No. 16/560,084, filed on Sep. 4, 2019, which is a continuation-in-part of application No. PCT/IL2018/050184, filed on Feb. 19, 2018.

(60) Provisional application No. 62/467,139, filed on Mar. 5, 2017.

(51) Int. Cl.
| | |
|---|---|
| *A61K 31/047* | (2006.01) |
| *A61K 9/00* | (2006.01) |
| *A61K 9/08* | (2006.01) |
| *A61K 47/32* | (2006.01) |
| *A61P 27/02* | (2006.01) |
| *A61P 27/04* | (2006.01) |
| *A61K 31/728* | (2006.01) |
| *A61K 47/34* | (2017.01) |

(52) U.S. Cl.
CPC .......... *A61K 31/047* (2013.01); *A61K 9/0048* (2013.01); *A61K 9/08* (2013.01); *A61K 47/32* (2013.01); *A61P 27/02* (2018.01); *A61P 27/04* (2018.01); *A61K 31/728* (2013.01); *A61K 47/34* (2013.01)

(58) Field of Classification Search
None
See application file for complete search history.

(56) References Cited

U.S. PATENT DOCUMENTS

| | | | |
|---|---|---|---|
| 5,106,615 | A | 4/1992 | Dikstein |
| 5,895,645 | A | 4/1999 | Dabrowski et al. |
| 6,060,486 | A | 5/2000 | Urashima et al. |
| 8,912,166 | B2 | 12/2014 | Dikstein |
| 9,278,132 | B2 | 3/2016 | Davio et al. |
| 2009/0111770 | A1 | 4/2009 | Holzer et al. |
| 2014/0057983 | A1* | 2/2014 | Dikstein ............... A61K 31/047 514/567 |
| 2014/0315836 | A1 | 10/2014 | Aizawa et al. |

FOREIGN PATENT DOCUMENTS

| | | |
|---|---|---|
| JP | H9301866 A | 11/1997 |
| WO | 9832421 A1 | 7/1998 |
| WO | 2006123324 A1 | 11/2006 |

OTHER PUBLICATIONS

Ciurtin et al ("Advances in the treatment of ocular dryness associated with Sjogren's syndrome", Seminars in Arthritis and Rheumatism, vol. 45(3), 2015, p. 321-327).*
Solomon et al ("The Effect of a New Tear Substitute Containing Glycerol and Hyaluronate on Keratoconjunctivitis Sicca", Journal of Ocular Pharmacology and Therapeutics, vol. 14(6), 1998, p. 497-504).*
Scrivanti et al (Syndrome sec oculaire: utilization d'un nouveau substitute lachrymal (LO2A), Ophthalmologie, vol. 10, 1996, p. 24-27).*
Bawazeer et al ("One-Minute Schirmer Test With Anesthesia", Cornea, vol. 22(4), 2003, p. 285-287).*
Kiss et al (Isotonic Glycerol and Sodium Hyaluronate Containing Artificial Tear Decreases Conjunctivochalasis after One and Three Months: A Self-Controlled, Unmasked Study, PloS ONE, vol. 10(7), 2015, p. 1-13).*
Abelson et al ("The Dye-namics of Dry-Eye Diagnosis", Review of Ophthalmology, published Nov. 15, 2005—an internet article obtained from the website https://www.reviewofophthalmology.com/article/the-dye-namics-of-dry-eye-diagnosis).*
Nemeth et al ("Lid-parallel conjunctival folds (LIPCOF) and dry eye: a multicentre study", British Journal of Ophthalmology, vol. 96(11), (2012), p. 1380-1385).*
Bawazeer et al., "One-Minute Schirmer Test With Anesthesia", Cornea, 2003, pp. 285-287, vol. 22:4.
Ciurtin et al., "Advances in the treatment of ocular dryness associated with Sjogren's syndrome", Seminars in Arthritis and Rheumatism, 2015, pp. 321-327, vol. 45.
Gensheimer et al., "Novel Formulation of Glycerin 1% Artificial Tears Extends Tear Film Break-Up Time Compared with Systane Lubricant Eye Drops", Journal of Ocular Pharmacology and Therapeutics, 2012, pp. 473-478, vol. 28:5.
Kiss et al., "Isotonic Glycerol and Sodium Hyaluronate Containing Artificial Tear Decreases Conjunctivochalasis after One and Three Months: A Self-Controlled, Unmasked Study", PLoS One, Jul. 15, pp. 1-13, vol. 35:85.
Modis, "Sjogren Ocular Disease Treatment", Clinical Therapeutics, 2013, pp. e121, vol. 35:85.
Scrivanti et al., "Dry-eye syndrome: hyaluronic acid eyedrop (LO2A)", Ophtalmologie, 1996, pp. 24-27, vol. 10.
Solomon et al., "The Effect of a New Tear Substitute Containing Glycerol and Hyaluronate on Keratoconjunctivitis Sicca", Journal of Ocular Pharmacology and Therapeutics, 1998, pp. 497-504, vol. 14:6.

(Continued)

*Primary Examiner* — Sin J Lee
(74) *Attorney, Agent, or Firm* — The Webb Law Firm

(57) ABSTRACT

A method for treatment of irritation or damage to corneal or conjunctival epithelial cells, particularly for irritation or damage to corneal or conjunctival epithelial cells due to severe Sjögren's syndrome, comprising applying topically to an affected eye an aqueous solution of glycerol characterized by a glycerol concentration of >1% (w/v), most preferably 2.5% (w/v). The method is effective even in the case of very low tear formation, and its effectiveness cannot be explained by the known humectant effect of glycerol.

15 Claims, No Drawings

(56) References Cited

OTHER PUBLICATIONS

Suvarna et al., "A Comprehensive Review on Dry Eye Disease: Diagnosis, Medical Management, Recent Developments, and Future Challenges", Advances in Pharmaceutics, Jan. 2015, pp. 1-12.

Cohen et al., "Evaluation of Clinical Outcomes in Patients with Dry Eye Disease Using Lubricant Eye Drops Containing Polyethylene Glycol or Carboxymethylcellulose," 2014, Clin. Ophthal. vol. 8, pp. 157-164.

Narayanan, "Which Drop for Dry Eye?," 2009, Rev. Optometry, vol. 146, No. 4, pp. 1-6.

O'Brien et al., "Dry Eye: Diagnosis and Current Treatment Strategies," 2004, Curr. Allergy Asthm. R., vol. 4, pp. 314-319.

Saeed et al., "Effectiveness of Sodium Hyaluronate Eye Gel in Patients with Dry Eye Disease: a Multi-centre, Open Label, Uncontrolled Study," 2013, Pak. J. Med Sci., vol. 29, pp. 1055-1058.

Aragona et al., "Sodium hyaluronate eye drops of different osmolarity for the treatment of dry eye in Sjogren's symdrome patients", British Journal of Ophthalmology, 2002, pp. 879-884, vol. 86.

\* cited by examiner

EYE DROPS FOR TREATMENT OF IRRITATION NOT DUE TO INFECTION

CROSS REFERENCE TO RELATED APPLICATIONS

This application is a continuation of U.S. patent application Ser. No. 16/560,084, filed Sep. 4, 2019, which is a Continuation-in-Part of PCT (International) Application No. PCT/IL2018/050184, filed Feb. 19, 2018, and claims priority to U.S. Provisional Patent Application No. 62/467,139, filed Mar. 5, 2017, each of which is incorporated by reference in their entirety.

FIELD OF THE INVENTION

This invention relates in general to means and methods for treatment and elimination of irritation to corneal or conjunctival epithelial tissue. In particular, it relates to the use of eye drops comprising a solution of glycerol in water for treating devitalized corneal or conjunctival epithelial cells such as are found in severe cases of Sjögren's syndrome.

BACKGROUND OF THE INVENTION

Corneal or conjunctival epithelial cell damage occurs in many corneal diseases such as dry eye disease; occupational dry eye caused by insufficient rate of blinking; lack of tear production such as is found, for example, in Sjögren's syndrome; Meibomian oil deficiency; drug or preservative induced cell damage; mechanical cell damage induced by such factors as contact lens wearing; and ocular surface disease.

Treatments for corneal or conjunctival epithelial cell damage known in the art tend to be strictly palliative and are generally aimed at lessening the severity of the symptoms of the condition rather than at treating the condition by healing the damaged cells. For example, mild cases of Sjögren's syndrome are normally treated by use of moisture replacement therapies such as by application of artificial tears, which have only limited effectiveness. More severe cases require more radical treatment such as the use of drugs that affect the immune system, which during chronic treatment lead to side effects in up to 20% of cases; see, for example, Ciurtin, C. et al., "Advances in the Treatment of Ocular Dryness Associated with Sjögren's Syndrome," *Semin. Arthritis Rheu.* 2015, 45, 321-317, and Modis, L. "Sjögren Ocular Disease Treatment," *Clin. Ther.* 2013, 35, e121-e122, both of which are incorporated by reference in their entirety.

U.S. Pat. No. 5,106,615, which is hereby incorporated by reference in its entirety, discloses humectant eye drops that are useful for treatment of dry eye syndrome. The eye drops have non-Newtonian rheological properties that mimic the behavior of natural tears, and comprise an aqueous solution of a low molecular weight humectant polyol at approximately isotonic concentration, an anionic polymer having a molecular weight between 500,000 and 4,000,000, and less than 1.5 mM inorganic salt.

U.S. Pat. No. 8,912,166 (henceforth '166), which is hereby incorporated by reference in its entirety, discloses an ophthalmic preparation and method for treating conjunctivochalasis, a disease of the conjunctival folds. The preparation comprises an aqueous solution of glycerol, a normal component of human blood. In contrast to artificial tear solutions known in the art, the preparation disclosed in '166 provides a statistically significant reduction in the severity of the condition as measured by the Lid Parallel Conjunctival Folds (LIPCOF) scale.

Despite these advances, compositions and methods for treating corneal irritation that heal the damaged cells rather than merely ease the symptoms, especially in severe cases of Sjögren's Syndrome, remain a long-felt, but as yet unmet need.

SUMMARY OF THE INVENTION

The present invention provides a method for treatment of irritated corneal or conjunctival epithelial cells in which the cell irritation is due to a cause other than infection. Irritation of the corneal and epithelial cells will lead to damage of those cells. The method of treatment disclosed herein at a minimum alleviates the severity of, and typically cures entirely, such cell damage. The treatment of the irritation leads to healing of the damaged tissue. The method comprises application of eye drops that contain glycerol as the sole active ingredient to treat the irritation. The present invention also discloses an ophthalmological composition for treatment of such conditions, and the use of the composition in the treatment thereof.

It is therefore an object of the present invention to disclose the use of an ophthalmic preparation comprising an aqueous solution of glycerol in a treatment comprising treatment or prevention of irritation of epithelial cells of the eye, wherein said aqueous solution comprises at least 1% (w/v) glycerol and said method comprises applying said ophthalmic preparation to an affected eye.

It is a further object of this invention to disclose such a use in a treatment of irritation of corneal epithelial cells.

It is a further object of the present invention to disclose such a use in a treatment for prevention of irritation of corneal epithelial cells.

It is a further object of the present invention to disclose such a use in a treatment of irritation of conjunctival epithelial cells, wherein said method comprises applying said ophthalmic preparation to an affected eye.

It is a further object of the present invention to disclose such a use in a treatment for prevention irritation to conjunctival epithelial cells, wherein said method comprises applying said ophthalmic preparation to an affected eye.

It is a further object of the present invention to disclose the use as defined in any of the above, wherein said irritation is not due to infection.

It is a further object of the present invention to disclose the use as defined in any of the above, wherein said treatment is a treatment of cell irritation resulting from a cause selected from the group consisting of Sjögren's syndrome, Meibomian oil deficiency, drug-induced cell irritation, preservative-induced cell irritation, mechanical cell irritation induced by contact lens wearing, and ocular surface disease.

It is a further object of the present invention to disclose the use as defined in any of the above, wherein said method comprises determining a level of devitalization of cells by using Rose Bengal staining.

It is a further object of the present invention to disclose the use as defined in any of the above, wherein said method comprises determining a level of devitalization of cells by using Lissamine Green staining.

It is a further object of the present invention to disclose the use as defined in any of the above, wherein said aqueous solution is characterized by a glycerol concentration of between 1.1% and 4% (w/v).

It is a further object of the present invention to disclose the use as defined in any of the above, wherein said aqueous solution is essentially isotonic.

It is a further object of the present invention to disclose the use as defined in any of the above, wherein said aqueous solution has a pH between 6.7 and 7.7.

It is a further object of the present invention to disclose the use as defined in any of the above, wherein said aqueous solution is characterized by an inorganic salt concentration of less than 0.1% w/v.

It is a further object of the present invention to disclose the use as defined in any of the above, wherein said aqueous solution comprises at least one polymer of molecular weight of at least 10,000 Dalton. In some preferred embodiments of the invention, the concentration of said polymer is chosen to bring said solution to a predetermined viscosity. In some particularly preferred embodiments of the invention, said viscosity is between 5 and 125 mPa·s. In some embodiments of the invention, said at least one polymer is anionic. In some preferred embodiments of the invention in which said at least one polymer is anionic, said solution comprises at least one polymer selected from the group consisting of hyaluronates, carbomers, and combinations and mixtures thereof.

It is a further object of the present invention to disclose the use as defined in any of the above, wherein said aqueous solution comprises a pharmaceutically effective amount of at least one pharmacologically active agent.

It is a further object of the present invention to disclose the use as defined in any of the above, wherein said aqueous solution comprises at least one substance selected from the group consisting of stabilizers, preservatives, antioxidants, and buffers.

It is a further object of the present invention to disclose the use as defined in any of the above, wherein said treatment comprises applying said ophthalmic preparation from three to eight times daily.

It is a further object of the present invention to disclose the use as defined in any of the above, wherein said treatment comprises applying said ophthalmic preparation until a statistically significant reduction in severity of irritation to corneal epithelial cells, as measured by Lissamine Green staining, is observed. In some embodiments of the invention, said treatment comprises applying said ophthalmic preparation three to eight times daily for a period of time not exceeding three months. In some embodiments of the invention, said treatment comprises applying said ophthalmic preparation three to eight times daily for a period of time not exceeding one month.

It is a further object of the present invention to disclose the use as defined in any of the above, wherein said treatment comprises applying prophylactically said ophthalmic preparation at predetermined intervals following completion of a therapeutic course of treatment, thereby maintaining a condition in which said irritation remains significantly reduced relative to its severity prior to said course of therapeutic treatment. In preferred embodiments of the invention, said treatment comprises applying prophylactically applying said ophthalmic preparation daily following a therapeutic course of treatment.

It is a further object of the present invention to disclose a method for treating irritation of corneal epithelial cells, wherein said method comprises applying an ophthalmic preparation comprising an aqueous solution of glycerol to an affected eye.

It is a further object of the present invention to disclose a method for preventing irritation of corneal epithelial cells, wherein said method comprises applying an aqueous solution of glycerol to an affected eye.

It is a further object of the present invention to disclose a method for treating irritation of conjunctival epithelial cells, wherein said method comprises applying an ophthalmic preparation comprising an aqueous solution of glycerol to an affected eye.

It is a further object of the present invention to disclose a method for preventing irritation of conjunctival epithelial cells, wherein said method comprises applying an aqueous solution of glycerol to an affected eye.

It is a further object of the present invention to disclose a method as defined in any of the above, wherein said irritation is not due to infection.

It is a further object of the present invention to disclose a method as defined in any of the above, wherein said method comprises treating cell irritation resulting from a cause selected from the group consisting of Sjögren's syndrome, Meibomian oil deficiency, drug-induced cell irritation, preservative-induced cell irritation, irritation due to mechanical cell damage induced by contact lens wearing, and ocular surface disease.

It is a further object of the present invention to disclose a method as defined in any of the above, comprising using Rose Bengal staining to determine a level of devitalization of cells due to irritation.

It is a further object of the present invention to disclose a method as defined in any of the above, comprising using Lissamine Green staining to determine a level of devitalization of cells due to irritation.

It is a further object of the present invention to disclose a method as defined in any of the above, wherein said step of applying an aqueous solution of glycerol comprises applying an aqueous solution of glycerol characterized by a glycerol concentration of between 1% and 4% (w/v).

It is a further object of the present invention to disclose a method as defined in any of the above, wherein said step of applying an aqueous solution of glycerol comprises applying an essentially isotonic aqueous solution of glycerol.

It is a further object of the present invention to disclose a method as defined in any of the above, wherein said step of applying an aqueous solution of glycerol comprises applying an aqueous solution of glycerol characterized by a pH between 6.7 and 7.7.

It is a further object of the present invention to disclose a method as defined in any of the above, wherein said step of applying an aqueous solution of glycerol comprises applying an aqueous solution of glycerol characterized by an inorganic salt concentration of less than 0.1% w/v.

It is a further object of the present invention to disclose a method as defined in any of the above, wherein said step of applying an aqueous solution of glycerol comprises applying an aqueous solution of glycerol comprising at least one polymer of molecular weight of at least 10,000 Dalton. In some preferred embodiments of the method, the concentration of said polymer is chosen to bring said solution to a viscosity of between 5 and 125 mPa·s. In some preferred embodiments of the method, said at least one polymer is anionic. In some preferred embodiments of the method in which said polymer is anionic, said at least one polymer is a hyaluronate. In some preferred embodiments of the method in which said polymer is anionic, said at least one polymer is a carbomer. In some preferred embodiments of the method in which said at least one polymer is anionic, said solution comprises at least one polymer selected from the group consisting of hyaluronates, carbomers, and combinations and mixtures thereof.

It is a further object of the present invention to disclose a method as defined in any of the above, wherein said step of applying an aqueous solution of glycerol comprises applying an aqueous solution of glycerol comprising a pharmaceutically effective amount of a pharmacologically active agent.

It is a further object of the present invention to disclose a method as defined in any of the above, wherein said step of applying an aqueous solution of glycerol comprises applying an aqueous solution of glycerol comprising a substance selected from the group consisting of stabilizers, preservatives, antioxidants, and buffers.

It is a further object of the present invention to disclose a method as defined in any of the above, wherein said method comprises applying said ophthalmic preparation from three to eight times daily.

It is a further object of the present invention to disclose a method as defined in any of the above, wherein said method comprises applying said ophthalmic preparation until a statistically significant reduction in the severity of irritation to corneal epithelial cells, as measured by Lissamine Green staining, is observed.

It is a further object of the present invention to disclose a method as defined in any of the above, wherein said method comprises applying said ophthalmic preparation three to eight times daily for a period of time not exceeding three months. In some preferred embodiments of the invention, said method comprises applying said ophthalmic preparation three to eight times daily for a period of time not exceeding one month.

It is a further object of the present invention to disclose a method as defined in any of the above, wherein said method comprises applying said ophthalmic preparation prophylactically following completion of a therapeutic course of treatment, thereby maintaining a condition in which said irritation remains significantly reduced relative to its severity prior to said course of therapeutic treatment. In preferred embodiments of the method, said step of applying said ophthalmic preparation prophylactically comprises applying said ophthalmic preparation daily.

It is a further object of this invention to disclose an ophthalmic preparation comprising an aqueous solution of glycerol, wherein said ophthalmic preparation comprises at least 1% (w/v) glycerol and is an effective treatment for treatment or prevention of irritation of epithelial cells of the eye.

It is a further object of this invention to disclose an ophthalmic preparation comprising an aqueous solution of glycerol, wherein said ophthalmic preparation is an effective treatment for prevention or treatment of irritation of conjunctival epithelial cells.

It is a further object of this invention to disclose an ophthalmic preparation as defined in any of the above, wherein said ophthalmic preparation is an effective treatment for prevention or elimination of irritation to corneal or conjunctival cells as measured by a method selected from the group consisting of Rose Bengal staining and Lissamine Green staining.

It is a further object of this invention to disclose an ophthalmic preparation as defined in any of the above, wherein said ophthalmic preparation is characterized by a glycerol concentration of between 1% and 4% (w/v).

It is a further object of this invention to disclose an ophthalmic preparation as defined in any of the above, wherein said solution is essentially isotonic.

It is a further object of this invention to disclose an ophthalmic preparation as defined in any of the above, wherein said solution has a pH between 6.7 and 7.7.

It is a further object of this invention to disclose an ophthalmic preparation as defined in any of the above, wherein said solution is characterized by an inorganic salt concentration of less than 0.1%.

It is a further object of this invention to disclose an ophthalmic preparation as defined in any of the above, comprising at least one polymer of molecular weight of at least 10,000 Dalton. In some preferred embodiments of the invention, the concentration of said at least one polymer is chosen to bring said solution to a predetermined viscosity. In some particularly preferred embodiments of the invention, said predetermined viscosity is between 5 and 125 mPa·s. In some preferred embodiments of the invention, said at least one polymer is anionic. In some preferred embodiments of the invention in which said at least one polymer is anionic, said solution comprises at least one polymer selected from the group consisting of hyaluronates, carbomers, and combinations and mixtures thereof.

It is a further object of this invention to disclose an ophthalmic preparation as defined in any of the above, comprising a pharmaceutically effective amount of at least one pharmacologically active agent.

It is a further object of this invention to disclose an ophthalmic preparation as defined in any of the above, comprising a substance selected from the group consisting of stabilizers, preservatives, antioxidants and buffers.

It is a further object of this invention to disclose the use of the ophthalmic preparation as defined in any of the above in a method as defined in any of the above.

It is a further object of this invention to disclose the use of an aqueous solution comprising at least 1% glycerol (w/v) in the preparation of a composition for treatment or prevention of irritation of epithelial cells of the eye. In some preferred embodiments of the invention, said treatment is selected from the group consisting of treatment of irritation of corneal epithelial cells; prevention of irritation of corneal epithelial cells; treatment of irritation of conjunctival epithelial cells; and prevention of irritation of conjunctival epithelial cells. In some preferred embodiments of the invention, said ophthalmic preparation is an effective treatment for prevention or elimination of irritation to corneal or conjunctival cells as measured by a method selected from the group consisting of Rose Bengal staining and Lissamine Green staining.

DETAILED DESCRIPTION OF THE PREFERRED EMBODIMENTS

In the following description, various aspects of the invention will be described. For the purposes of explanation, specific details are set forth in order to provide a thorough understanding of the invention. It will be apparent to one skilled in the art that there are other embodiments of the invention that differ in details without affecting the essential nature thereof. In some cases, for clarity or conciseness, individual components or method steps of the invention are described separately. Nonetheless, any combination of individual elements or method steps that are disclosed herein that is not self-contradictory is considered by the inventor to be within the scope of the invention.

As used herein, the term "severe Sjögren's Syndrome" refers to Sjögren's Syndrome characterized by a 1-minute Schirmer Test of 2 mm or less (see Bawazeer, A. M.; Hodge, W. G., "One-Minute Schirmer Test with Anesthesia," *Cornea* 2003, 22, 285-287, which is hereby incorporated by reference in its entirety).

The inventor has discovered that surprisingly, glycerol is an effective substance for treatment of irritation of corneal epithelial cells, irritation of conjunctival epithelial cells, and hence, damage to conical or conjunctival cells when these conditions are caused by factors other than infection, even in the complete absence of tear formation, such as is found in severe Sjögren's Syndrome. Topical application of glycerol (e.g. in an aqueous solution) to the affected eye reduces or even eliminates entirely conical or conjunctival irritation without increasing the rate of tear formation.

The invention herein disclosed is an ophthalmic preparation for treatment or prevention of irritation to corneal or conjunctival epithelial cells, in particular, for treatment of irritation to corneal or conjunctival epithelial cells resulting from severe Sjögren's Syndrome, the preparation comprising an aqueous glycerol solution having a concentration of greater than 1% glycerol (w/v). In typical embodiments of the invention, the solution comprises 1.1%-4% glycerol (w/v). In some preferred embodiments of the invention, the solution comprises 2.5% glycerol (w/v). In preferred embodiments of the invention, the solution is isotonic.

In preferred embodiments of the invention, the composition comprises an aqueous glycerol solution in which the concentration of inorganic salts is less than 2 mM. In preferred embodiments of the invention, the viscosity of the solution is controlled by addition of a quantity of high molecular weight polymer (MW>$10^4$ Dalton) such as hyaluronate, carbomer or a mixture thereof, sufficient to bring the solution to the desired viscosity. All ingredients are of purity sufficient for use in eye drops.

The solutions may then be transferred to a container appropriate for dispensing it as eye drops.

While in some embodiments of the invention, the only active ingredient present in the composition is glycerol, the composition may comprise in addition a pharmaceutically effective concentration at least one pharmacologically active agent. If necessary, any stabilizer, preservative, antioxidant, buffer or combination thereof appropriate for use with the pharmacologically active agent may be added to the solution in any concentration suitable for use in eye drops.

It is within the scope of the invention to disclose the use of the eye drops in the non-surgical treatment of, or prevention of, irritation of and irritation to the conical or conjunctival epithelial tissue, particularly damage due to causes other than infection, and a method of non-surgical treatment or prevention of irritation of and hence, damage to the corneal or conjunctival epithelial tissue, particularly damage due to causes other than infection. Non-limiting examples of conditions that can be treated by the eye drop composition disclosed herein include Sjögren's syndrome, Meibomian oil deficiency, drug or preservative induced irritation, irritation due to mechanical cell damage such as cell damage induced by contact lens wearing, and ocular surface disease.

A typical protocol for use of the eye drops disclosed herein to treat or to alleviate corneal and/or conjunctival epithelial cell damage is to place drops in the affected eye three to eight times daily until the severity of condition is reduced to an acceptable level. In particularly severe cases, more frequent applications may be necessary, and in less severe cases, one or two daily treatments may be sufficient. The progress of the treatment can be measured by the use of techniques such as Lissamine Green staining or Rose Bengal staining to track the condition of the epithelial cells. In some preferred embodiments of the treatment, application of the composition disclosed herein is performed for no more than three months, by which time statistically significant improvement of the condition of the conical or conjunctival epithelial cells is observed. In some preferred embodiments of the treatment, application of the composition disclosed herein is performed for no more than one month, by which time statistically significant improvement of the condition of the corneal or conjunctival epithelial cells is observed.

It is within the scope of the invention to include within the method prophylactic application of the composition disclosed herein in order to prevent recurrence of the condition. After the course of therapeutic treatment, which typically lasts no more than three months, a maintenance regimen comprising prophylactic application of the eye drops is begun. Application of the eye drops one to three times daily is usually sufficient to prevent recurrence of the irritation.

In contrast to methods known in the art, in particular, those that use drugs that affect the immune system, no side effects were observed in any of the treatment protocols in which the invention disclosed herein was tested. In particular, no side effects were observed with long-term use of eye drops containing as much as 2.5% (w/v) glycerol.

The following examples of the preparation and use of the ophthalmological composition herein disclosed are intended to assist a person having ordinary skill in the art to make and use the invention, and are not to be construed as being in any way limiting.

Example 1

Anti-Irritation Eye Drops

A solution was prepared containing:

| | |
|---|---|
| Glycerol | 2.5 g |
| Carbomer 981 | 0.05 g |
| Water | to 100 ml |

The solution was buffered to a pH of 7.2.

Example 2

Anti-Irritation Eye Drops

A solution was prepared containing:

| | |
|---|---|
| Glycerol | 2.5 g |
| Sodium hyaluronate | 0.015 g |
| Carbomer 981 | 0.015 g |
| Water | to 100 ml |

The solution was adjusted to a pH of approximately 7.

Example 3

Anti-Glaucoma Eye Drops

A solution was prepared containing:

| | |
|---|---|
| Glycerol | 2.5 g |
| Latanoprost | 5 mg |
| Carbomer 981 | 0.03 g |
| Water | to 100 ml |

The solution was adjusted to pH of between 6.8 and 7.6. A suitable concentration of preservative may optionally be added.

Example 4

A composition was prepared as described in Example 2 above and was tested on 21 patients suffering from severe Sjögren's syndrome. Results of the study are summarized in Table 1; the value in each column is the mean score with the standard error of the mean given in parentheses. Lissamine Green staining evaluated by Oxford Grade is a measure of the severity of dry eye syndrome, while OSDI (Ocular Surface Disease Index) is a measure of patient satisfaction. At the conclusion of the treatment, the patients' eyes were free of measurable damage.

TABLE 1

| Time | Oxford Grade | OSDI Index |
|---|---|---|
| Initial | 1.86 (0.1) | 55.8 (3.2) |
| 1 month | 0.85 (0.21) | 37.7 (4.3) |
| 3 months | 0.25 (0.13) | 32.5 (4.2) |

These results are surprising and unexpected, since the Schirmer's test, which measures the level of tear formation was very low at the start of the study (1.6±0.3 mm) and did not change significantly after 3 months of treatment (1.7±0.3 mm). That is, in the patients treated according to the method herein disclosed, using the composition herein disclosed, objective measures of the level of eye irritation symptomatic of Sjögren's Syndrome due to the severely reduced tear production characteristic of the condition showed a significant decrease, even though the very low level of tear production did not increase. This observation cannot be explained by the known physicochemical moisturizing effect of glycerol.

Example 5

An experiment was performed to investigate the effect in vitro of a solution containing glycerol on human corneal epithelial cells, in particular, on the expression of barrier genes Involucrin, Occludin, Filaggrin, and Cadherin-1.

Immortalized human corneal epithelial cells (HCEC cell line) cultured in DMEM/F12 with 5% FBS and 10 ng/ml human epidermal growth factor (Invitrogen—Gibco). The cells were treated for three hours with one of the following three compositions: (a) an aqueous solution of glycerol (0.27% w/v); (b) 20 μg/ml Polyinosinic:polycytidylic acid (p(I:C), an activator of TLR3 to induce inflammation; and (c) a combination of the two previous compositions.

The expression of the barrier genes was determined at the mRNA level by use of quantitative "real-time" PCR (Q-PCR). Q-PCR was performed on an ABI Prism 7000 sequence detection system (Applied Biosystems, Foster City, Calif.) using the 5' nuclease assay. Total RNA was isolated using TRIzol (Invitrogen) and 3 μg of total RNA were reverse-transcribed into cDNA by using 15 U of AMV reverse transcriptase (Promega, Madison, Wis., USA) and 0.025 μg/μl random primers (Promega). PCR amplification was performed by using the TaqMan primers and probes. As internal controls, transcripts of cyclophilin A (PPIA) were determined.

The pro-inflammatory challenge p(I:C) (20 μg/ml) markedly decreased the expressions of Involucrin, Occludin, Filaggrin, and Cadherin-1. However, of greatest importance, co-incubation of the human corneal epithelial cells with glycerol (0.27%) during the p(I:C)challenge significantly prevented the barrier-impairing actions of the TLR3 agonist.

These results indicate the pro-differentiating, barrier-repairing, anti-inflammatory and protective effects of glycerol on human corneal epithelial cells. Without wishing to be bound by theory, the results of this experiment may help explain the surprising results observed in the treatment protocol described in the previous example.

Example 6

A study was performed in which twelve commercially available artificial tear formulations were applied to the eyes of patients suffering from Sjögren's syndrome according to the package direction. Treatment periods varied from 2 months to over a year. In no case was any improvement in the condition of the eyes observed. The results of the studies are summarized in Table 2. Letters in parentheses indicate treatment of different patients using the same formulation.

TABLE 2

| Composition | Active ingredient(s) | length of use |
|---|---|---|
| 1 | dextran, hydroxypropylmethylcellulose | (a) >1 year |
|   |   | (b) 6 months |
| 2 | Zinc hyaluronate | 3 months |
| 3 | polyethylene glycol 400, propylene glycol, hydroxypropyl-guar | (a) 1 month |
|   |   | (b) 3 months |
|   |   | (c) 6 months |
| 3a | Similar to 3 | (a) 3 months |
|   |   | (b) 6 months |
| 4 | Tetrahydrozoline HCl | (a) 3 months |
|   |   | (b) 3 months |
| 5 | hypertonic saline solution | (a) 2 months |
|   |   | (b) 1 month |
| 5a | preservative-free version of 5 | >1 year |
| 6 | Benzalkonium chloride, Alcohol, Glycerin (<1%), Witch hazel | 2 months |
| 7 | sodium carboxymethylcellulose | (a) 2 months |
|   |   | (b) 3 months |
| 8 | Propylene Glycol 0.6% | 3 months |
| 9 | Hypromellose 2.5% | >1 year |
| 10 | 50 mg dexapanthenol & polyacrylic polymer | 2 months |
| 11 | Naphazoline Hydrochloride | >1 year |
| 12 | Polyvinyl Alcohol | >1 year |

Example 7

A study was performed comparing the efficacy of the instant invention to that of hyaluronate-containing humectant eye drops known in the prior art. Sixteen patients suffering from severe dry eye due to Sjögren's syndrome were treated for one month with eye drops containing 0.15% hyaluronic acid as the active ingredient, followed by treatment for one month with eye drops prepared according to the formula given in Example 2 above (i.e. containing both hyaluronic acid and 2.5% (w/v) glycerol). The results are summarized in Table 3.

TABLE 3

| | enrollment | 1 month | 2 month | enrollment Test | 1 month | 2 month |
|---|---|---|---|---|---|---|
| | od | | | os | | |
| LIPCOF[a] | 2.75 ± 0.11 | 2.69 ± 0.12 | 1.625 ± 0.125 | 2.81 ± 0.125 | 2.625 ±0.125 | 1.625 ± 0.154 |
| Oxford | 3.56 ± 0.22 | 3.19 ± 0.21 | 1.69 ± 0.12 | 3.625 ± 0.22 | 3.31 ± 0.24 | 1.625 ± 0.125 |
| Schirmer[b] | 0.50 ± 0.18 | 0.56 ± 0.16 | 0.50 ± 0.13 | 0.56 ± 0.16 | 0.56 ± 0.18 | 0.63 ± 0.18 |
| BUT[c] | 2.98 ± 0.27 | 4.60 ± 0.29 | 4.67 ± 0.28 | 2.92 ± 0.24 | 4.60 ± 0.27 | 4.56 ± 0.29 |
| OSDI | 63.4 ± 3.2 | | 44.9 ± 4.0 | | | 31.6 ± 3.2 |

[a]Lid Parallel Conjunctival Folds scale (0 = least severe, 3 = most severe)
[b]1-minute Schirmer test (mm)
[c]Tear breakup time (s)

As can be seen from the results summarized in the table, eye drops containing hyaluronic acid as the sole active ingredient did not produce any significant change in the objective LIPCOF and Oxford measurements. In contrast, the values of these measurements returned nearly to normal within a month of treatment using the glycerol-containing eye drops of the invention disclosed herein, even though the level of tear production, as measured by the Schirmer test, remained very low. The subjective OSDI parameter was also significantly improved following treatment with the eye drops of the invention disclosed herein.

These results further demonstrate that the effectiveness of eye drops containing 2.5% glycerol as a treatment for severe Sjögren's syndrome cannot be attributed solely to the known humectant effect of glycerol.

I claim:

1. A method for treating irritation or damage to conjunctival or corneal epithelial cells resulting from Sjögren's syndrome, said method comprising:
characterizing said Sjögren's syndrome by a method selected from the group consisting of:
determining a LIPCOF score; and,
determining a level of devitalization of said conjunctival or corneal epithelial cells by a method selected from the group consisting of Rose Bengal staining and Lissamine Green staining;
further characterizing said Sjögren's syndrome by a value representing a level of tear production as measured by a Schirmer's test;
applying at predetermined intervals to an affected eye an ophthalmic preparation comprising an aqueous solution comprising glycerol and a substance selected from the group consisting of hyaluronic acid and hyaluronate; wherein:
said step of applying an ophthalmic preparation comprises applying at predetermined intervals said ophthalmic preparation to an affected eye until at least one condition selected from the group consisting of:
said LIPCOF score is statistically significantly lowered without any statistically significant change in said value of said Schirmer's test measurement; and,
a statistically significant reduction in the level of devitalization of said conjunctival or corneal epithelial cells, as measured by said Lissamine Green or Rose Bengal staining, is observed, without any statistically significant change in said value of said Schirmer's test measurement;
is met; and,
said ophthalmic preparation is characterized by a glycerol concentration of between 1.1% and 4% (w/v) and a concentration of said substance selected from the group consisting of hyaluronic acid and hyaluronate of 0.015% (w/v).

2. The method according to claim 1, wherein said method is a method for treating irritation or damage to conjunctival or corneal epithelial cells resulting from severe Sjögren's syndrome.

3. The method according to claim 1, wherein said aqueous solution is essentially isotonic.

4. The method according to claim 1, wherein said aqueous solution has a pH of between 6.7 and 7.7.

5. The method according to claim 1, wherein said aqueous solution has an inorganic salt concentration of less than 0.1% w/v.

6. The method according to claim 1, wherein said aqueous solution is selected from the group consisting of:
an aqueous solution comprising between 1.1% and 4% (w/v) glycerol and 0.015% (w/v) hyaluronate, said hyaluronate characterized by a molecular weight of at least 10,000 Dalton;
an aqueous solution comprising between 1.1% and 4% (w/v) glycerol, 0.015% (w/v) hyaluronate, and a polymer characterized by a molecular weight of at least 10,000 Dalton; and,
an aqueous solution comprising between 1.1% and 4% (w/v) glycerol, 0.015% (w/v) hyaluronate, and a polymer, said hyaluronate and said polymer both characterized by a molecular weight of at least 10,000 Dalton.

7. The method according to claim 6, wherein the concentration of said polymer is chosen to bring said aqueous solution to a viscosity of between 5 and 125 mPa·s.

8. The method according to claim 6, wherein said polymer is a carbomer.

9. The method according to claim 1, wherein said aqueous solution comprises a pharmaceutically effective amount of a pharmacologically active agent.

10. The method according to claim 1, wherein said aqueous solution further comprises stabilizers, preservatives, antioxidants, or buffers.

11. The method according to claim 1, wherein said ophthalmic preparation consists of an aqueous solution consisting of 2.5% glycerol (w/v), 0.015% sodium hyaluronate (w/v), 0.015% carbomer 981 (w/v), a sufficient amount of acid or base to adjust said solution to a pH of between 6.7 and 7.7, and the balance water.

12. The method according to claim 11, wherein said ophthalmic preparation consisting of said aqueous solution is applied to said eye affected by said Sjögren's syndrome as characterized by a value of 1.6±0.3 mm for the level of tear production as measured by a one-minute Schirmer's test.

13. The method according to claim 1, wherein said method comprises applying said ophthalmic preparation from three to eight times daily.

14. The method according to claim 13, wherein said method comprises applying said ophthalmic preparation three to eight times daily for a period of time not exceeding three months.

15. The method according to claim 1, wherein said method further comprises applying said ophthalmic preparation prophylactically following completion of a therapeutic course of the treatment of the irritation or damage to the conjunctival or corneal epithelial cells.

* * * * *